United States Patent
Xing et al.

(10) Patent No.: US 11,948,676 B2
(45) Date of Patent: Apr. 2, 2024

(54) QUALITATIVE AND QUANTITATIVE MRI USING DEEP LEARNING

(71) Applicant: The Board of Trustees of the Leland Stanford Junior University, Stanford, CA (US)

(72) Inventors: Lei Xing, Palo Alto, CA (US); Yan Wu, Los Altos, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 409 days.

(21) Appl. No.: 17/265,697

(22) PCT Filed: Dec. 12, 2019

(86) PCT No.: PCT/US2019/065946
§ 371 (c)(1),
(2) Date: Feb. 3, 2021

(87) PCT Pub. No.: WO2020/123788
PCT Pub. Date: Jun. 18, 2020

(65) Prior Publication Data
US 2021/0313046 A1     Oct. 7, 2021

Related U.S. Application Data

(60) Provisional application No. 62/779,486, filed on Dec. 14, 2018.

(51) Int. Cl.
*G16H 30/20*     (2018.01)
*A61B 5/055*     (2006.01)
(Continued)

(52) U.S. Cl.
CPC .............. *G16H 30/40* (2018.01); *A61B 5/055* (2013.01); *G06N 3/08* (2013.01); *G16H 30/20* (2018.01)

(58) Field of Classification Search
CPC ....................................................... A61B 5/055
See application file for complete search history.

(56) References Cited

U.S. PATENT DOCUMENTS

| 10,062,014 B2 | 8/2018 | Zhou |
| 2018/0084988 A1* | 3/2018 | Chakravorty ........ A61B 5/7275 |

(Continued)

FOREIGN PATENT DOCUMENTS

| WO | WO2018048507 | 3/2018 |
| WO | WO2018200493 | 11/2018 |

OTHER PUBLICATIONS

Qing Lyu, Ge Wang, Quantitative MRI—Absolute T1, T2 and Proton Density Parameters from Deep Learning, Biomedical Imaging Center CBIS/BME/SoE, Rensselaer Polytechnic Institute Troy, NY, USA Jun. 2018.

(Continued)

*Primary Examiner* — Di Xiao

(57) ABSTRACT

A method for quantitative magnetic resonance imaging (MRI) includes [800] performing an MRI scan using a conventional pulse sequence to obtain a qualitative MR image; and [802] applying the qualitative MR image as input to a deep convolutional neural network (CNN) to produce a quantitative magnetic resonance (MR) relaxation parametric map. The qualitative MR image is the only image input to the deep neural network to produce the quantitative MR relaxation parametric map. The conventional pulse sequence may be a Spoiled Gradient Echo sequence, a Fast Spin Echo sequence, a Steady-State Free Precession sequence, or other sequence that is commonly used in current clinical practice.

8 Claims, 7 Drawing Sheets

(51) Int. Cl.
G06N 3/08 (2023.01)
G16H 30/40 (2018.01)

(56) References Cited

U.S. PATENT DOCUMENTS

| | | | |
|---|---|---|---|
| 2018/0144467 A1 | 5/2018 | Sofka | |
| 2018/0199815 A1* | 7/2018 | Redei | G16B 20/20 |
| 2018/0217217 A1* | 8/2018 | Weingartner | G01R 33/50 |
| 2018/0292484 A1 | 10/2018 | Hoppe | |
| 2019/0025393 A1* | 1/2019 | Ng | G01R 33/58 |
| 2019/0033418 A1* | 1/2019 | Haacke | G01R 33/56554 |
| 2019/0139259 A1* | 5/2019 | Zhang | G06T 11/60 |
| 2019/0219653 A1* | 7/2019 | Shiodera | G01R 33/54 |
| 2020/0311914 A1* | 10/2020 | Zaharchuk | G06V 10/82 |
| 2021/0033688 A1* | 2/2021 | Koch | G01R 33/56 |

OTHER PUBLICATIONS

West et al., Novel whole brain segmentation and volume estimation using quantitative MRI, Jonathan H West, J B M Warntjes, Peter LundbergPublished 2011 in European RadiologyDOI:10.1007/s00330-011-2336-7.
Bhavya Shah et al., "Quantitative MR Imaging: Physical Principles and Sequence Design in Abdominal Imaging" RadioGraphics 2011; 31:867-880, Published Online:May 4, 2011.
Coppo et al., Overview of Magnetic Resonance Fingerprinting. MAGNETOM Flash I (65) Feb. 2016.
He et al. Identity Mappings in Deep Residual Networks. Jul. 25, 2016 URL: https://arxiv.org/abs/1603.05027.

* cited by examiner

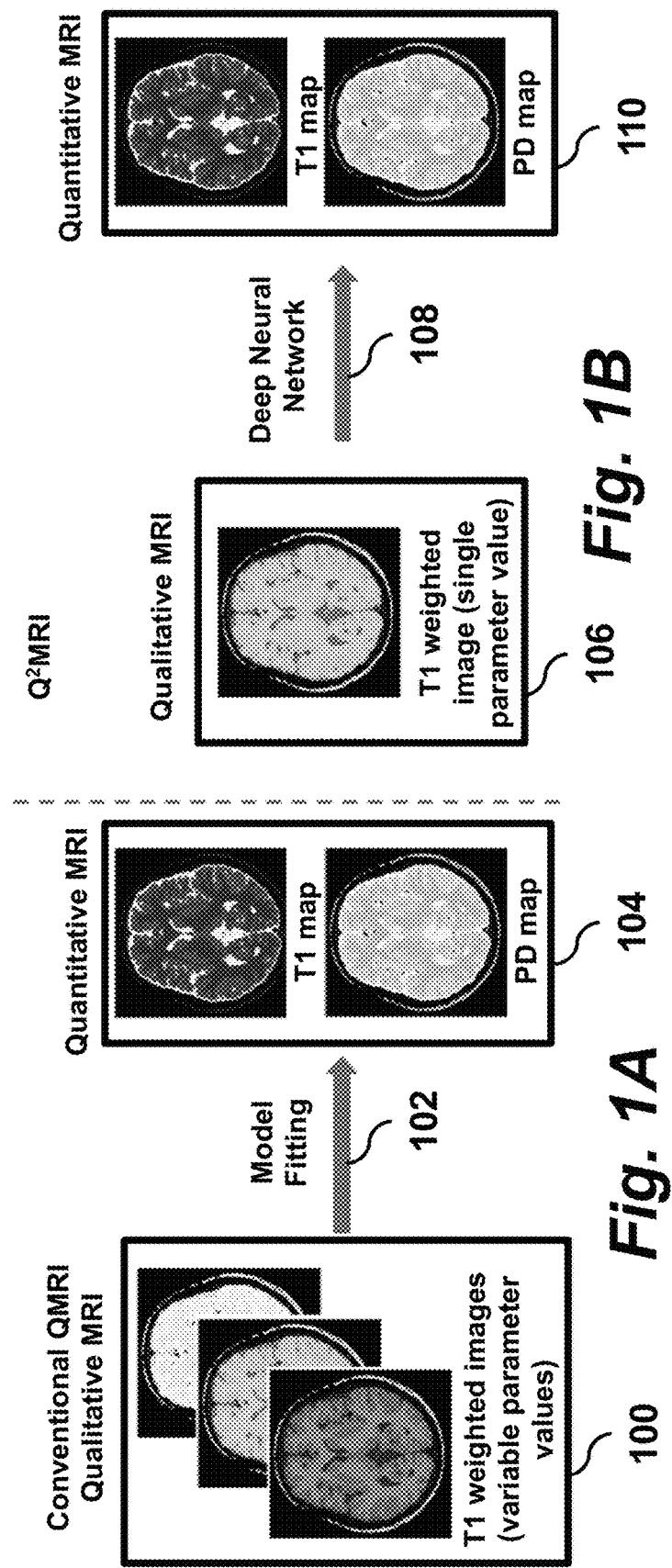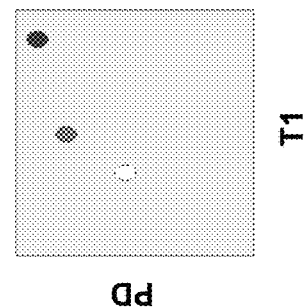

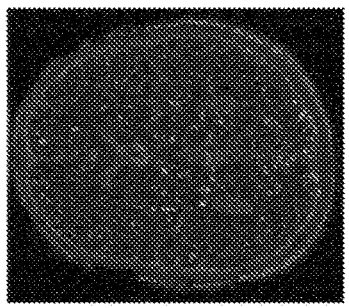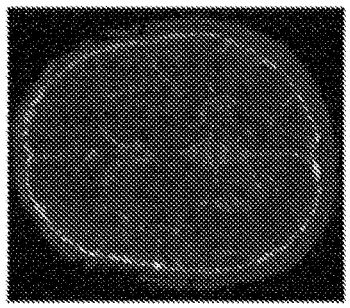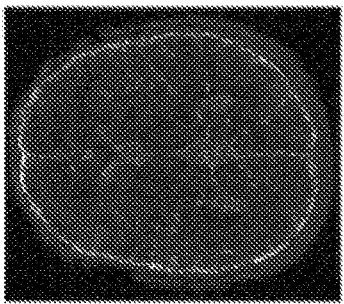
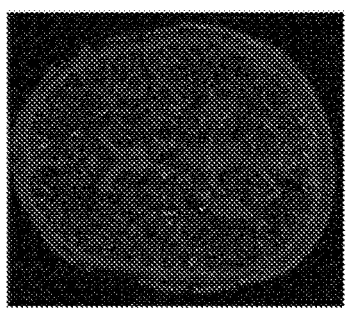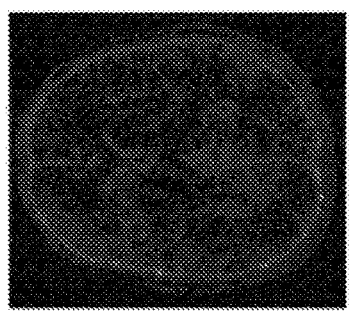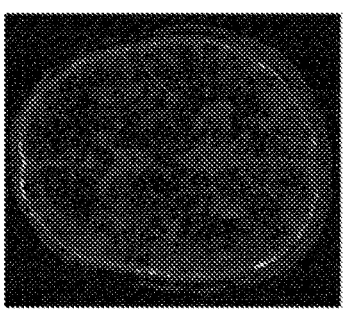
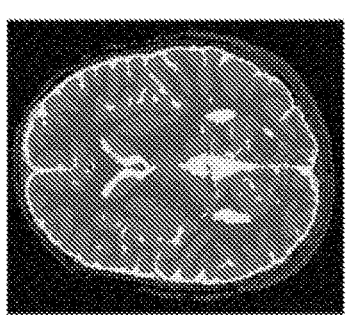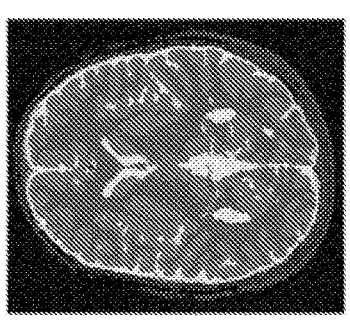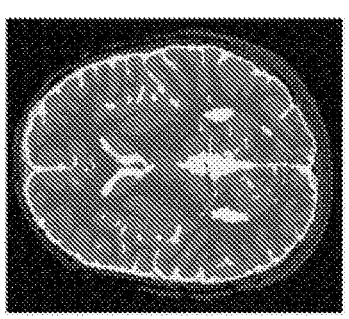
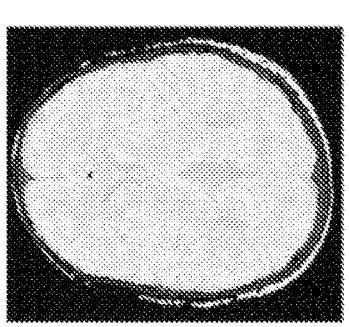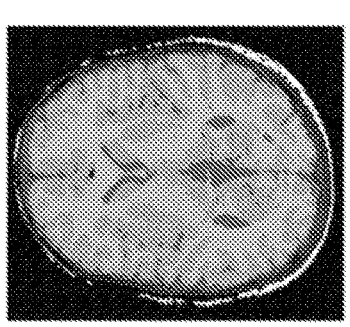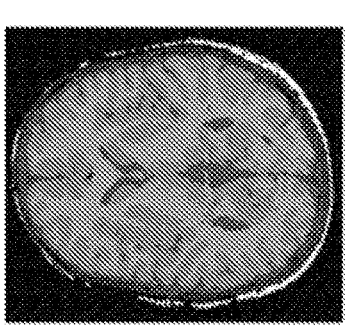
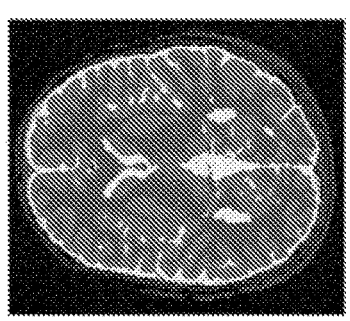
Fig. 5A  Fig. 5B  Fig. 5C  Fig. 5D  Fig. 5E

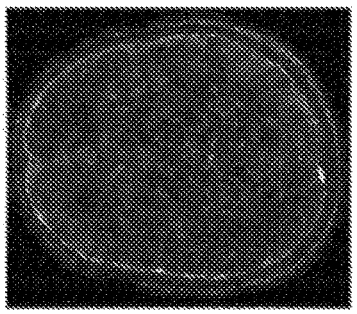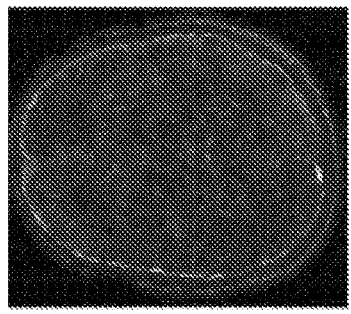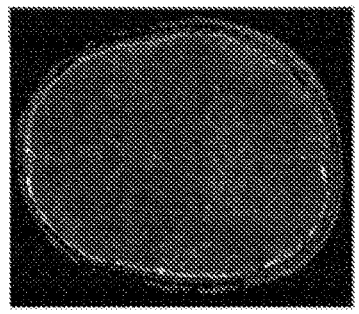
*Fig. 6E*
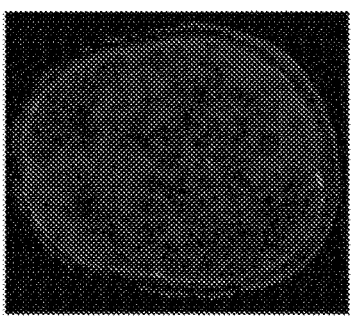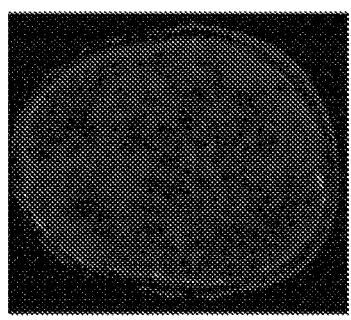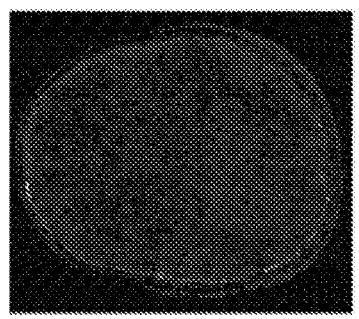
*Fig. 6D*
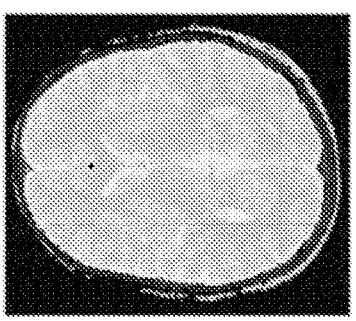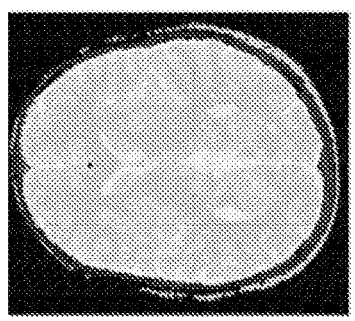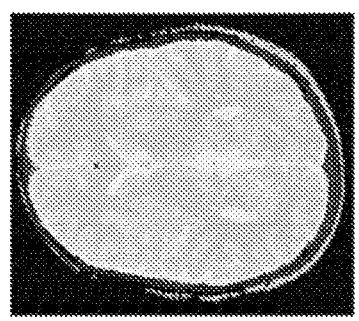
*Fig. 6C*

*Fig. 6B*
*Fig. 6A*

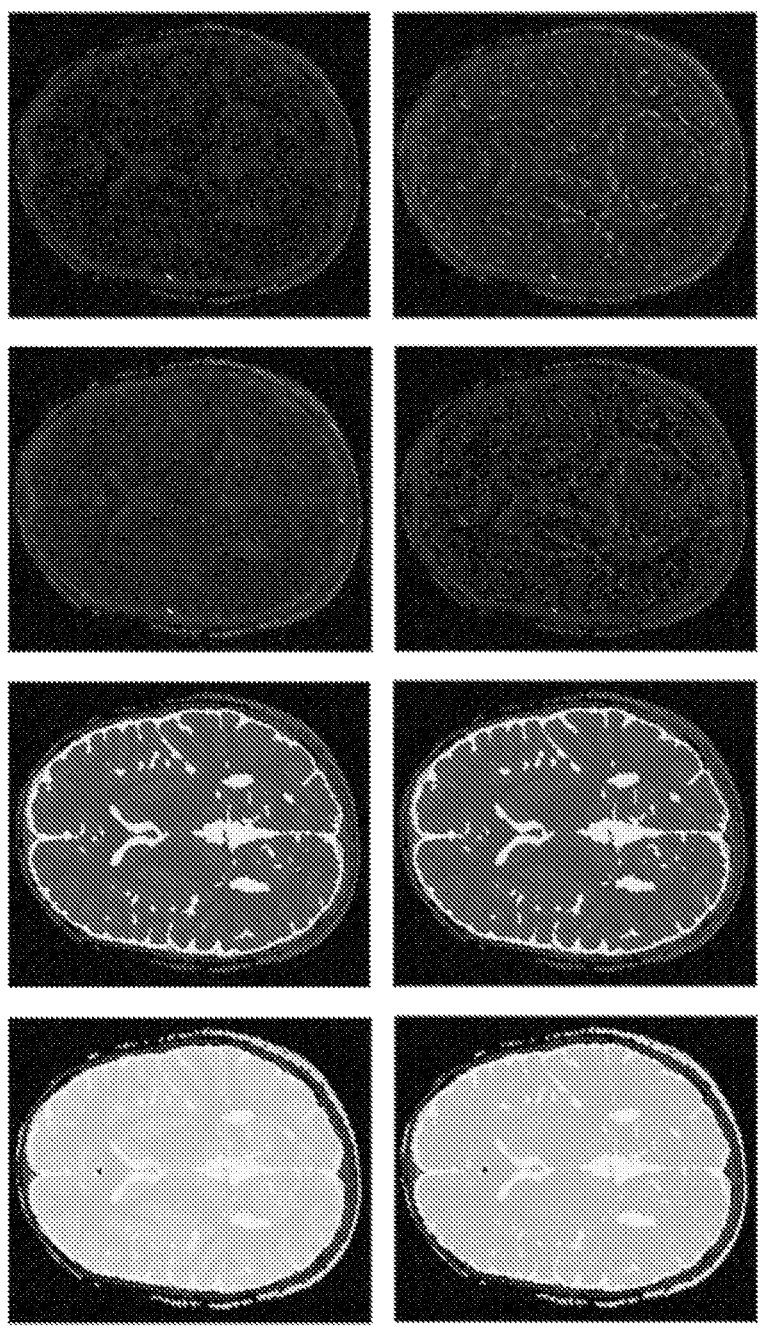
Fig. 7A  Fig. 7B  Fig. 7C  Fig. 7D  Fig. 7E

QUALITATIVE AND QUANTITATIVE MRI USING DEEP LEARNING

CROSS-REFERENCE TO RELATED APPLICATIONS

This application is a 371 of PCT application PCT/US2019/065946 filed Dec. 12, 2019. PCT application PCT/US2019/065946 claims the benefit of U.S. Provisional application 62/779,486 filed Dec. 14, 2018.

FIELD OF THE INVENTION

The present invention relates generally to diagnostic imaging. More specifically, it relates to methods for quantitative magnetic resonance imaging (MRI).

BACKGROUND OF THE INVENTION

In conventional clinical MRI, a qualitative magnetic resonance (MR) image with a specific weighting ($T_1$ weighting, $T_2$ weighting, or other) is acquired using a particular value of every imaging parameter (time of repetition, echo time, flip angle, etc.). The signal intensity of resulting qualitative images depends on the imaging parameter values specified in the imaging protocol, which may vary from hospital to hospital.

Quantitative MRI involves measurement of inherent tissue relaxation properties ($T_1$ relaxation time, $T_2$ relaxation time, proton density). Unlike qualitative MR images, quantitative MR relaxation parametric maps are independent of operator-specific imaging parameters and are valuable for a variety of applications. While qualitative MR images are used for conventional diagnosis, additional quantitative relaxation parametric maps provide extra information for tissue characterization and treatment response assessment. By measuring tissue relaxation properties that are changed by pathology, quantitative MRI helps to diagnose diseases with higher specificity than qualitative MRI. Furthermore, because the signal intensity of quantitative MRI is independent of the pulse sequence and imaging parameters, quantitative MRI supports data sharing across different medical centers whose protocols for image acquisition may be different.

Traditionally, a quantitative MR image (or map) is obtained from multiple qualitative MR images that are acquired with different values of parameters (time of repetition, echo time, flip angle, spin-lock time) to gain variable contrasts, as conducted in the variable flip angle method, DESPOT$_1$ and DESPOT$_2$ approach. The signal intensity for each image is determined by the imaging parameters selected for the scan. Multiple qualitative images are generally required for the acquisition of a quantitative MRI map in order to ensure adequate sampling of signal evolution and, therefore, accurate measurement of relaxation times. Thus, quantitative MRI requires multiple time-consuming qualitative MRI scans with different imaging parameters, which is prohibitively long scan time for clinical applications.

Alternatively, MR fingerprinting is a technique for quantitative MRI that allows multiple quantitative parametric maps to be derived from a single image. The MR fingerprinting technique uses a special pulse sequence where imaging parameter values are changed in a pseudo-random manner during a single scan. Unfortunately, this additional pulse sequence requires changes in standard clinical imaging protocols, which would adversely impact the routine clinical practice.

SUMMARY OF THE INVENTION

Contrary to conventional wisdom, the inventors have discovered that, surprisingly, it is possible to obtain a quantitative MR relaxation parametric map ($T_1$, $T_2$, or proton density maps) from a single qualitative MR image obtained using standard imaging protocols. This realization is unexpected in view of the conventional understanding that, using standard imaging protocols, multiple scans with different imaging parameters are necessary to obtain quantitative information of tissue relaxation properties ($T_1$ relaxation time, $T_2$ relaxation time, proton density).

The disclosed method allows a single MRI acquisition using a conventional pulse sequence (i.e. Spoiled Gradient Echo sequence, Fast Spin Echo sequence, or Steady State Free Precession sequence) to provide both a qualitative image and quantitative parametric maps. Quantitative MR relaxation parametric maps can be produced from a single conventional qualitative MR image acquired in clinical practice without elongating MRI scan time. Thus, for the first time, quantitative MRI parametric maps can be obtained without changing standard clinical imaging protocols, i.e., performing multiple scans with imaging parameter values changed.

The disclosed method uses deep learning to derive quantitative MR parametric maps from a single qualitative MR image acquired with standard imaging protocol. This surprising result is possible from the discovery that statistical and spatial a priori information (statistical relationship between various tissue relaxation properties as well as spatial continuity of an individual tissue relaxation parametric map) can be learned by neural networks and then used to provide a mapping from a qualitative MR image to quantitative relaxation parametric maps. Using such networks, a single qualitative image is input to deep convolutional neural networks without requiring input of any additional MR images of the subject. The neural networks output quantitative MRI parametric map(s) of $T_1$ relaxation, $T_2$ relaxation, and/or proton density.

The disclosed method includes particular neural network architectures that provide significant performance benefits such as making network training faster and more accurate. Preferably, the network is a hierarchical convolutional neural network with residual learning. The input and ground truth data used to train the network may be simulated data or real data.

In a standard clinical imaging protocol, qualitative images are acquired using a conventional pulse sequence, which can be a Spoiled Gradient Echo sequence, Fast Spin Echo sequence, Steady State Free Precession sequence, or other sequence that is commonly used in current clinical practice. For example, a $T_1$ weighted image is typically acquired using the Spoiled Gradient Echo sequence. This single qualitative image is then applied to the neural networks to derive the corresponding quantitative $T_1$ map and proton density map without taking additional scans. Similarly, a $T_2$ map can be produced either from a single $T_2$ weighted image acquired using the Spoiled Gradient Echo sequence or the Spin Echo (Carr-Purcell-Meiboom-Gill) sequence, or from a $T_2/T_1$ weighted image acquired using the Steady State Free Precession sequence, which are included in standard clinical imaging protocols. Also, in a standard clinical imaging protocol, imaging parameter values are not changed during a single scan.

Instead of conventional exponential fitting from a series of qualitative images, the deep convolutional neural network provides an end-to-end mapping from a single qualitative MR image to corresponding quantitative MR relaxation parametric maps, taking advantage of statistical and spatial a priori information. In this way, qualitative and quantitative MR images can be obtained in the routine clinical practice with one scan using standard imaging protocol which acquires a $T_1$ weighted or $T_2$ weighted image. Using this approach, large amount of quantitative MR data will be generated from conventional MRI, benefiting both prospective and retrospective studies.

In one aspect, the invention provides a method for quantitative magnetic resonance imaging (MRI) comprising: performing an MRI scan using a conventional pulse sequence to obtain a qualitative MR image; and applying the qualitative MR image as input to a deep convolutional neural network (CNN) to produce a quantitative magnetic resonance (MR) relaxation parametric map; wherein the qualitative MR image is the only image input to the deep neural network to produce the quantitative MR relaxation parametric map. Performing the MRI scan may include using a Spoiled Gradient Echo sequence, a Fast Spin Echo sequence, a Steady-State Free Precession sequence, or other sequences that are commonly used in current clinical practice. The parametric map may be a $T_1$ relaxation map, a $T_2$ relaxation map, a proton density map, or other quantitative map (e.g. magnetization transfer map), which is measured using a conventional quantitative imaging approach (such variable flip angle method, $DESPOT_1$ and $DESPOT_2$ approach).

The method may include applying the qualitative MR image as input to multiple deep convolutional neural networks to produce as output multiple quantitative MR relaxation parametric maps.

The deep neural network may be a hierarchical convolutional neural network with residual learning. The deep neural network may include downsampling and upsampling using convolution operations. The deep neural network may include local and global shortcut connections that facilitate residual learning and compensate for details lost in downsampling. The deep neural network may include shortcut connections, where pointwise addition is used, where nonlinear activation is applied before the pointwise addition and identity mapping is conducted after the pointwise addition. The deep neural network may include an attention mechanism.

BRIEF DESCRIPTION OF THE DRAWINGS

FIGS. 1A-B are schematic diagrams illustrating the acquisition of quantitative $T_1$ map and proton density map (FIG. 1A) from multiple qualitative $T_1$ weighted MR images using conventional model fitting, and (FIG. 1B) from a single qualitative $T_1$ weighted MR image using deep convolutional neural networks according to an embodiment of the invention.

FIG. 2 is a graph showing how the joint distribution of $T_1$ and proton density is clustered, according to an embodiment of the invention.

FIG. 4A shows quantitative relaxation parametric maps are generated. The mean values of $T_1$, $T_2$, and proton density are assigned for each type of tissue in the segmented regions specified by digital brain phantoms. Variations are introduced. FIG. 4B shows a $T_1$ weighted image is generated for $T_1$ mapping, using the SPGR sequence with given $T_1$ and proton density maps. FIG. 4C shows a $T_2/T_1$ weighted image is generated for $T_2$ mapping, using the SSFP sequence with given $T_1$, $T_2$ and proton density maps.

FIG. 5A-E show images illustrating prediction of quantitative $T_1$ map from a $T_1$ weighted image using T-net, according to an embodiment of the invention. At each row, a single $T_1$ weighted image acquired using a specific flip angle (2°, 10°, or 18°) was used to derive the quantitative $T_1$ map. FIG. 5A shows the true $T_1$ map, FIG. 5B shows the $T_1$ weighted image, FIG. 5C shows the predicted $T_1$ map, FIG. 5D shows the associate error map which was the absolute difference between the prediction and ground truth, and FIG. 5E shows the rescaled error map that amplified the error. High fidelity was achieved between the prediction and the ground truth.

FIG. 6A-E show images illustrating prediction of quantitative proton density (PD) map from a $T_1$ weighted image using T-net, according to an embodiment of the invention. At each row, a single $T_1$ weighted image acquired using a specific flip angle (2°, 10°, or 18°) was used to derive the quantitative PD map. FIG. 6A shows the true PD map, FIG. 6B shows the $T_1$ weighted image, FIG. 6C shows the predicted PD map, FIG. 6D shows the associate error map which was the absolute difference between the prediction and ground truth, and FIG. 6E shows the rescaled error map that amplified the error. High fidelity was achieved between the prediction and the ground truth.

FIG. 7A-E shows images illustrating prediction of quantitative $T_2$ map from a single $T_2/T_1$ weighted image using T-net, according to an embodiment of the invention. At each row, a single $T_2/T_1$ weighted SSFP image acquired using a specific flip angle (15° or 30°) was used to derive the quantitative $T_2$ map. FIG. 7A shows the true $T_2$ map, FIG. 7B shows the $T_2/T_1$ weighted SSFP image, FIG. 7C shows the predicted $T_2$ map, FIG. 7D shows the associate error map which was the absolute difference between the prediction and ground truth, and FIG. 7E shows the rescaled error map that amplified the error. High fidelity was achieved between the prediction and the ground truth.

DETAILED DESCRIPTION

Figure 3:
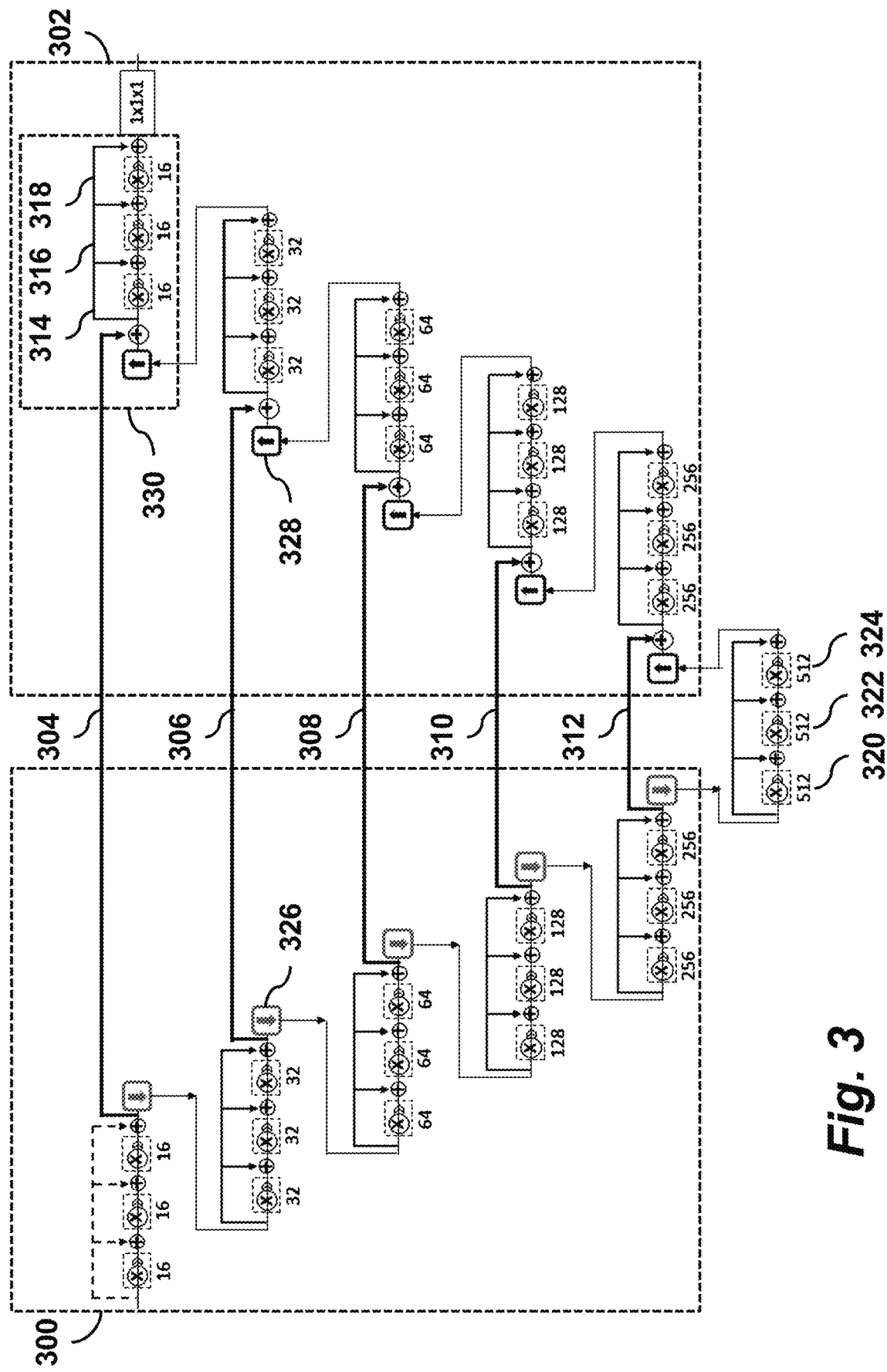
FIG. 3 is a schematic block diagram showing the hierarchical architecture of the deep convolutional neural network, according to an embodiment of the invention. The network is composed of a contracting path (on the left) and a subsequent expanding path (on the right), along which the resolution of feature maps first shrinks and then expands. Global shortcut connections are established between the same levels of the two paths to compensate for details lost in downsampling, whereas local shortcut connections are established within the same level of a single path to facilitate residual learning.

Preferred embodiments of the present invention provide methods for the acquisition of quantitative MRI that measures tissue properties ($T_1$, $T_2$, proton density). In existing $T_1$ mapping, a series of multiple $T_1$-weighted images 100 are acquired and model fitting 102 is performed for the quantification of parameters of interest to generate quantitative parameter maps 104, as illustrated in FIG. 1A. In this existing approach, multiple $T_1$ weighted images 100 are required to calculate the value of $T_1$ or proton density because signal intensity depends on both $T_1$ and proton density. Therefore, a series of $T_1$ weighted images 100 are acquired with the value of a specific imaging parameter (e.g. flip angle, inversion time, or time of repetition) being different among the images.

However, the inventors have discovered that deep learning enables the acquisition and utilization of generic a priori information to predict quantitative MRI data from a single qualitative MR image. We have discovered that $T_1$ and proton density, when viewed as random variables, are not independent, but closely correlated. Their joint distribution is clustered in the probability space, as illustrated in FIG. 2. The interdependency between these variables provides a useful constraint for the quantification of the parameters. In addition, location information aids in the derivation of quantitative map, where spatial continuity of individual relaxation parameters is taken advantage of. Using a deep neural network, both statistical and spatial a priori information can be nicely integrated, and the sophisticated mapping from qualitative MRI to quantitative MRI is searched in a higher dimensional space. During training, an inverse mapping is learned by the network to produce from a single $T_1$ weighted image the corresponding $T_1$ map and proton density map.

For $T_1$ mapping, the method uses a deep neural network 108 to derive quantitative $T_1$ and proton density maps no from a single conventional $T_1$ weighted image 106 acquired in routine clinical practice, as illustrated in FIG. 1B. With the use of the deep neural network, only one $T_1$ weighted image 106 is required for the generation of a quantitative $T_1$ map.

Similarly, a $T_2$ map can be produced from a single $T_2$ or $T_2/T_1$ weighted image using a trained deep neural network. In this way, qualitative and quantitative MR images can be obtained in the routine clinical practice without changing the imaging protocol or performing multiple scans.

The method may be performed by a conventional MRI scanner using standard imaging protocols, adapted with a neural network to generate the quantitative MRI map(s) from the qualitative image acquired by the scanner using conventional clinical imaging techniques. The deep learning network derives quantitative relaxation parametric maps from a single qualitative MR image, which gives flexibility to input qualitative images. The network may be implemented in the MRI scanner or on an external computer Nvidia GPU GeForce GTX1070.

Pulse sequences included in standard clinical imaging protocols may be used for acquisition of the qualitative image. For $T_1$ mapping, $T_1$ weighted images can be acquired using the Spoiled Gradient (SPGR) sequence. For $T_2$ mapping, $T_2/T_1$ weighted images can be obtained using the Steady State Free Precession (SSFP) sequence, or $T_2$ weighted images can be obtained using the Fast Spin Echo image (FSE) sequence. These examples are not intended to be exhaustive. The techniques of the present invention can also work with qualitative images acquired using various other standard pulse sequences.

Figure 8:
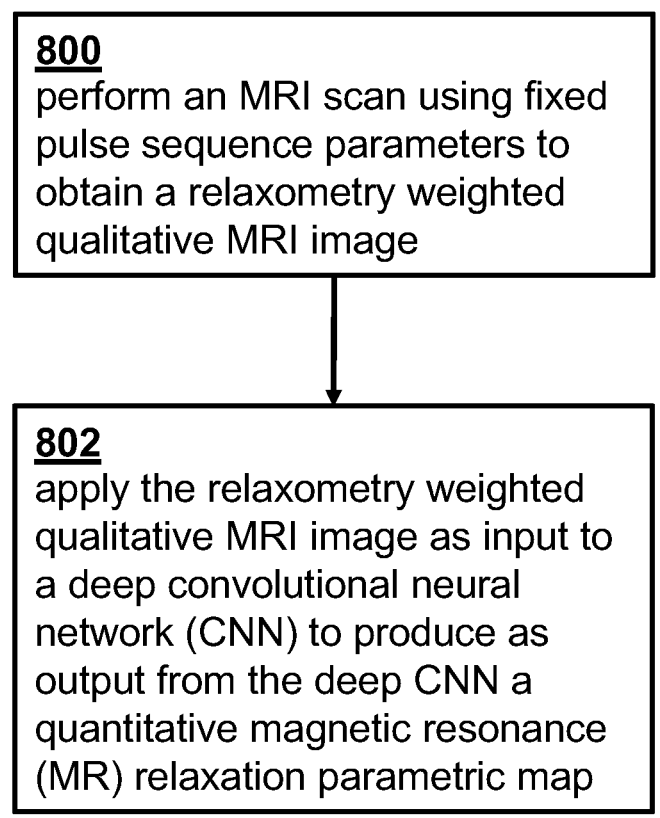
FIG. 8 is a flowchart illustrating an overview of a method of quantitative MRI according to an embodiment of the invention.

In a clinical setting, after a qualitative image is acquired 800 it is then applied 802 as input to the neural network to obtain the quantitative image, as shown in FIG. 8.

Training

The network is trained with input qualitative images and ground truth output quantitative images. The training set can be derived from volunteer and patient data using conventional quantitative MRI techniques. For each subject, a series of qualitative MR images are acquired with variable imaging parameter values, and corresponding quantitative MR maps are calculated via exponential fitting or other advanced techniques such as model-based reconstructions with a generating function, so as to obtain more accurate quantitative maps.

Figures 4A, 4B, 4C:
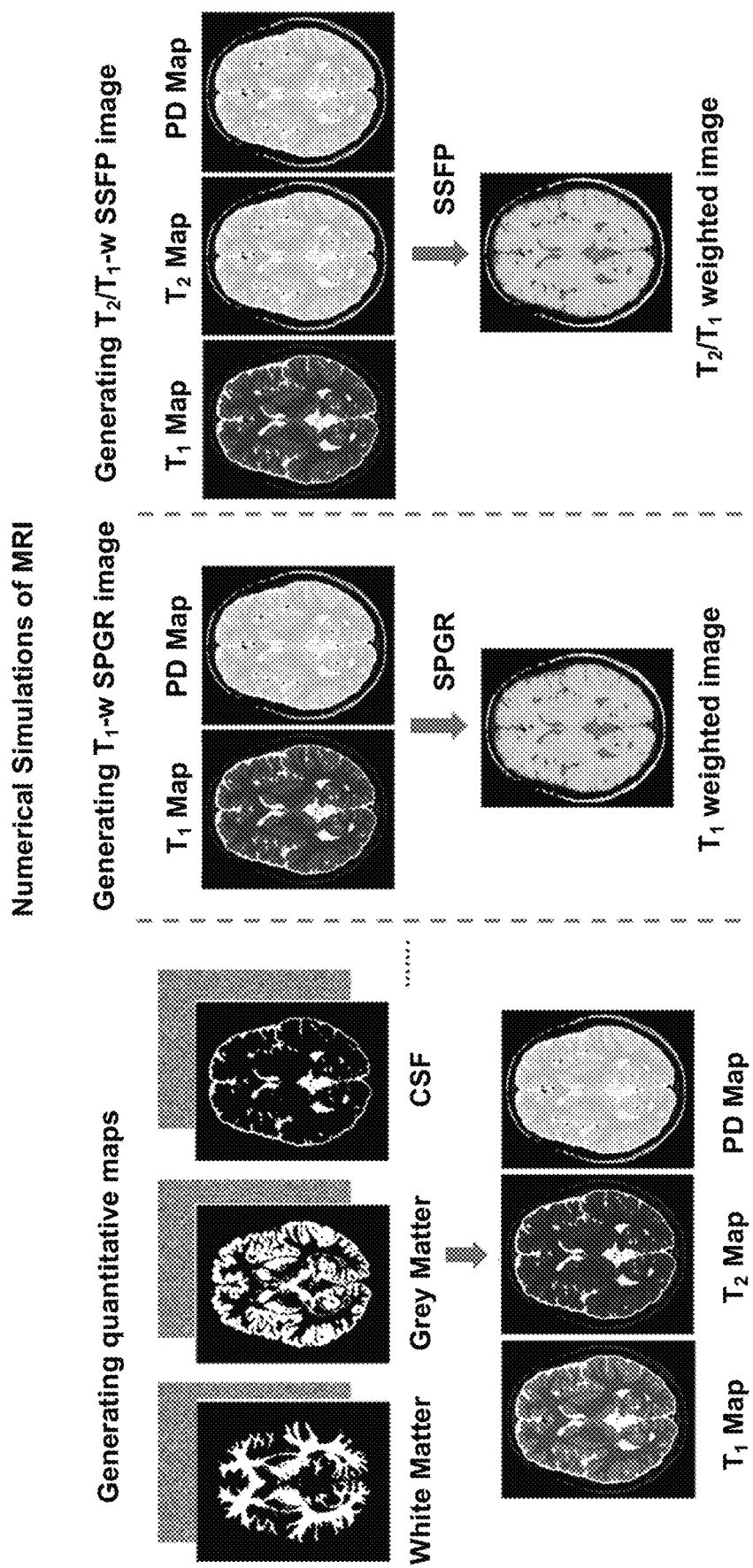
FIG. 4A-C illustrate numerical simulations for training and testing, according to an embodiment of the invention.

Alternatively, for proof of concept, the training set can be generated using simulations, where the quantitative maps are first simulated, then qualitative images were generated from the quantitative MRI maps using a particular choice of imaging parameters. There are different ways to generate qualitative MR images from given quantitative maps according to the Bloch equations. One way is to use the signal intensity equation for a specific sequence. Another way is to use the extended phase graph, where more factors can be taken into consideration (e.g. magnetic field inhomogeneities, partial volume effect). In a simulation study, quantitative MR parametric maps were first simulated as the ground truth, and qualitative MR images were subsequently generated by analytical calculation based on the equations of signal intensity or numerical simulation based on the Bloch equation. Digital brain phantoms were used to simulate quantitative multi-parametric maps ($T_1$, $T_2$ and proton density maps). Given those maps, MRI signals were generated, assuming the SPGR sequence was applied to acquire $T_1$ weighted images (for $T_1$ mapping), and the SSFP sequence was utilized to obtain $T_2/T_1$ weighted images (for $T_2$ mapping). This procedure is illustrated in FIG. 4A, FIG. 4B, and FIG. 4C. In FIG. 4A, quantitative relaxation parametric maps are generated. The mean values of $T_1$, $T_2$, and proton density are assigned for each type of tissue in the segmented regions specified by digital brain phantoms. Variations are introduced. In FIG. 4B, a $T_1$ weighted image is generated for $T_1$ mapping, using the SPGR sequence with given $T_1$ and proton density maps. In FIG. 4C, a $T_2/T_1$ weighted image is generated for $T_2$ mapping, using the SSFP sequence with given $T_1$, $T_2$ and proton density maps.

In the experiment, the networks were trained with 5792 two-dimensional images from 17 digital brain phantoms and tested with 1448 two-dimensional images from the remaining 3 digital brain phantoms. In fact, three different networks were established for the prediction of $T_1$ map, proton density map, and $T_2$ map, respectively. These networks had the same hyper-parameters but different parameters (as learned in training).

The optimal parameters of the neural networks are learned by iteratively minimizing the discrepancy between the prediction and ground truth, where the Root Mean Squared Error (RMSE) is defined as the loss function. With errors backpropagated, parameters at all levels are updated using the Adam optimization method with an adaptive learning rate (starting from 0.001, halved every 2000 iterations), $\beta_1$ of 0.9, $\beta_2$ of 0.999, and $\in$ of $10^{-8}$. Batch normalization is applied with a mini-batch size of ten images. In the training of the neural network, the Root Mean Squared Error (RMSE) decreased rapidly. This nice convergence behavior of the large-scaled neural network was attributed to the deep hierarchical architecture with embedded residual learning. The correlation coefficient between the prediction and the ground truth may be calculated for quantitative training performance evaluation.

Network Architecture

A neural network implementing the methods of the invention preferably has a hierarchical network architecture that enables the extraction of feature maps at different scales. This results in increased receptive fields (a wider range of context information) that provides valuable statistical and spatial information for the synthesis of quantitative MRI signal. Convolutional neural networks or generative adversarial networks with various architectures may be used. In a preferred embodiment, a hierarchical deep residual convolutional neural network (T-net) is used, as illustrated in FIG. 3.

The network is composed of an encoder 300 and a subsequent decoder 302, along which the resolution of feature maps first shrinks and then expands, respectively. The encoder 300 is a contracting path with the resolution of feature maps reduced, and the decoder 302 is an expanding path with the resolution of feature maps increased, each having six hierarchical levels, with downsampling between the encoder levels (e.g., downsampling 326) and upsampling between the decoder levels (e.g., upsampling 328). A bridging level 320 joins the encoder and decoder sections.

At every level, there are three convolutional blocks (e.g., blocks 320, 322, 324 of bridging level 320), where each block is composed of a convolutional layer that extracts feature maps with 3×3 kernels, and a nonlinear activation layer implemented by the PReLU function. The number of convolutional filters used in each subsequent layer is doubled after each down-sampling and halved after each up-sampling. Both downsampling and upsampling are accomplished using convolution operations (instead of conventional pooling function) with 2×2 kernels and a stride of 2.

Global shortcut connections 304, 306, 308, 310, 312, are established between the same levels of the encoder and decoder sections, whereas local shortcut connections are established within the individual levels (e.g., local shortcut connections 314, 316, 318 in the last level 330 of the decoder 302). The local and global shortcut connections facilitate residual learning and compensate for details lost in downsampling, respectively. Relatively dense local shortcut connections were constructed by forwarding the input of a hierarchical level to all the subsequent convolutional blocks at the same hierarchical level. This was inspired by the fact that dense connections significantly improved the network performance. However, dense connections, which forward the output of every convolutional block to all the subsequent blocks, are computationally expensive for high resolution image sets. We only forward the input of a hierarchical level to all the subsequent convolutional blocks at the same hierarchical level, reaching a good balance between the network performance and computational workload. For the shortcut connections, pointwise addition is adopted, where nonlinear activation is applied before the addition and identity mapping is conducted after the addition.

The invention as conceived by the inventors is not limited to the specific network architecture described above. The architecture of the preferred embodiment is designed to provide improved performance over other deep learning architectures, but the method does not depend upon this specific architecture to function. For example, other deep neural networks could be adopted, such as generative adversarial networks (GANs), which were widely explored for image generation. More advanced deep learning techniques can be incorporated as well, such as using cycle consistency loss in a GAN, integrating the attention mechanism into a deep neural network, etc. All these deep neural networks established an end-to-end mapping with performance superior to conventional methods.

Experiments were performed with simulated images to validate the methods of the present invention. The predicted quantitative MR relaxation parametric maps had high fidelity to the ground truth. Moreover, the method had low sensitivity to the imaging parameter values. Using different flip angles did not make apparent difference in the predicted maps. Therefore, when the method is applied to generate quantitative maps from a single qualitative MR image, a variety of imaging protocols can be adopted to obtain the qualitative relaxation parametric maps. Consequently large amount of quantitative MR data can be obtained from conventional MR images in retrospective studies as well as in retrospective prospective studies.

The network was able to predict quantitative $T_1$ map from a single $T_1$ weighted image with high fidelity, as shown in FIG. 5A, FIG. 5B, FIG. 5C, FIG. 5D, FIG. 5E. The ground truth $T_1$ map is shown in FIG. 5A.

FIG. 5B shows the $T_1$ weighted image acquired using SPGR, FIG. 5C shows the predicted $T_1$ map from the single $T_1$ weighted image, FIG. 5D shows the associate error map which was the absolute difference between the prediction and the ground truth, and FIG. 5E shows the rescaled error map that amplified the error. The error was minor in all the cases. The three rows of FIGS. 5A-E correspond to flip angles of 2°, 10°, and 18°, respectively, that were used to acquire a $T_1$ weighted SPGR image, which was the only source for the prediction of corresponding $T_1$ map.

In addition, high correlation coefficients were achieved between the predicted $T_1$ maps and the ground truth, which confirmed the high accuracy of the method. The results were stable when different qualitative images were obtained with variable imaging parameters, which demonstrated the robustness of the method.

Similarly, a T-net was established to predict quantitative proton density map from a single $T_1$ weighted image with high fidelity, as shown in FIG. 6A, FIG. 6B, FIG. 6C, FIG. 6D, FIG. 6E. The ground truth proton density map is shown in FIG. 6A. FIG. 6B shows $T_1$ weighted image acquired using SPGR with a specific flip angle, FIG. 6c shows predicted proton density map from the single $T_1$ weighted image, FIG. 6D shows associate error map which was the absolute difference between the prediction and the ground truth, and FIG. 6E shows rescaled error map that amplified the error. The error was minor. The three rows of FIGS. 6A-E correspond to flip angles of 2°, 10°, and 18°, respectively. Again, high correlation coefficients were achieved between the predicted proton density maps and the ground truth when variable imaging parameters were adopted, indicating high accuracy and robustness.

Another separately trained T-net achieved high accuracy in the prediction of quantitative $T_2$ map from a single $T_2/T_1$ weighted image, as shown in FIG. 7A, FIG. 7B, FIG. 7C, FIG. 7D, FIG. 7E. At each row of FIGS. 7B-7E, a specific flip angle (15°, or 30°) was used to acquire a $T_2/T_1$ weighted SSFP image, which was the only source for the prediction of corresponding $T_2$ map. FIG. 7A is the ground truth $T_2$ map, FIG. 7B shows the $T_2/T_1$ weighted image acquired using SSFP with a specific flip angle, FIG. 7C shows the predicted $T_2$ map from the single SSFP image, FIG. 7D shows the associate error map which was the absolute difference between the prediction and the ground truth, and FIG. 7E shows the resealed error map that amplified the error. The error was minor for both flip angles. In addition, high correlation coefficients were achieved between the predicted $T_2$ maps and the ground truth, which confirmed the high accuracy of the technique. The stability of the results (obtained with variable imaging parameters) further demonstrated robustness.

Discussion

In contrast to common knowledge and common practice, a single qualitative MR image is sufficient for the derivation of the quantitative maps. The approach allows us to obtain quantitative image information without the overhead of employing addition pulse sequences, which would otherwise change the current clinical imaging protocol and elongate the scan time. When imaging organs that are affected by respiratory or cardiac motions, the strategy of taking a single qualitative image as the only input successfully eliminates the necessity of image registration, which otherwise would be required to align various images for quantitative map generation.

We emphasize that the technique described has no special requirements on the pulse sequence and imaging parameters utilized. In this study, the SPGR and SSFP sequences were adopted for $T_1$ mapping and $T_2$ mapping due to the popularity of quantitative approaches $DESPOT_1$ and $DESPOT_2$ as well as the availability of those sequences in clinical imaging protocol. However, the technique can also work with other pulse sequences applicable for quantitative MRI (e.g. the Fast Spin Echo sequence used for $T_2$ mapping), since the mapping was automatically learned in training (as defined by network parameters) rather than analytically specified based on signal evolution. The method also had low sensitivity to the imaging parameters adopted. In the simulations conducted in this study, using various flip angles made only slight differences in the predicted quantitative maps. Therefore, various imaging protocols can be adopted to obtain input qualitative MRI for the derivation of quantitative maps. Consequently, large amount of quantitative MR data can be generated from conventional MRI in prospective m studies as well as in retrospective studies.

As a quantitative MRI approach, the techniques of the present invention differ from MR fingerprinting (MRF) in several aspects. First, MRF maps have inherently low spatial resolution, since all data points in a time frame are sampled within one relaxation time; In contrast, parameter maps generated by techniques of the present invention, which are transformed from conventional MR images, do not have this limitation. Secondly, the techniques of the present invention do not require modification of current clinical imaging protocols; In contrast, MRF uses a special pulse sequence that requires randomly changing imaging parameters during the scan. Thirdly, techniques of the present invention allow derivation of a single parametric map with standard scan time; In contrast, MRF acquires several parametric maps simultaneously at the cost of elongated scan time, which might provide more information than necessary.

The invention claimed is:

1. A method for quantitative magnetic resonance imaging (MRI) comprising: performing an MRI scan using a conventional pulse sequence to obtain a qualitative MR image; and applying the qualitative MR image as input to a deep convolutional neural network (CNN) to produce a quantitative magnetic resonance (MR) relaxation parametric map; wherein the qualitative MR image is the only image input to the deep neural network to produce the quantitative MR relaxation parametric map; further comprising applying the qualitative MR image as input to multiple deep convolutional neural networks to produce as output multiple quantitative MR relaxation parametric maps.

2. The method of claim 1 wherein performing the MRI scan includes using a Spoiled Gradient Echo sequence, a Fast Spin Echo sequence, or a Steady-State Free Precession sequence.

3. The method of claim 1 wherein the parametric map is a $T_1$ relaxation map, a $T_2$ relaxation map, a proton density map, or magnetization transfer map.

4. The method of claim 1 wherein the deep neural network comprises a hierarchical convolutional neural network with residual learning.

5. The method of claim 1 wherein the deep neural network includes downsampling and upsampling using convolution operations.

6. The method of claim 1 wherein the deep neural network includes an attention mechanism.

7. A method for quantitative magnetic resonance imaging (MRI) comprising: performing an MRI scan using a conventional pulse sequence to obtain a qualitative MR image; and applying the qualitative MR image as input to a deep convolutional neural network (CNN) to produce a quantitative magnetic resonance (MR) relaxation parametric map; wherein the qualitative MR image is the only image input to the deep neural network to produce the quantitative MR relaxation parametric map; wherein the deep neural network includes local and global shortcut connections that facilitate residual learning and compensate for details lost in downsampling.

8. A method for quantitative magnetic resonance imaging (MRI) comprising: performing an MRI scan using a conventional pulse sequence to obtain a qualitative MR image; and applying the qualitative MR image as input to a deep convolutional neural network (CNN) to produce a quantitative magnetic resonance (MR) relaxation parametric map; wherein the qualitative MR image is the only image input to the deep neural network to produce the quantitative MR relaxation parametric map; wherein the deep neural network includes shortcut connections, where pointwise addition is used, where nonlinear activation is applied before the pointwise addition and identity mapping is conducted after the pointwise addition.

* * * * *